United States Patent
Struble

(10) Patent No.: US 6,580,946 B2
(45) Date of Patent: Jun. 17, 2003

(54) PRESSURE-MODULATED RATE-RESPONSIVE CARDIAC PACING

(75) Inventor: Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 145 days.

(21) Appl. No.: 09/842,147

(22) Filed: Apr. 26, 2001

(65) Prior Publication Data

US 2002/0188329 A1 Dec. 12, 2002

(51) Int. Cl.⁷ .................................................. A61N 1/18
(52) U.S. Cl. ........................................................ 607/23
(58) Field of Search ...................... 607/23, 24; 600/374, 600/485, 508

(56) References Cited

U.S. PATENT DOCUMENTS

| | | | |
|---|---|---|---|
| 4,003,379 A | | 1/1977 | Ellinwood |
| 4,316,472 A | | 2/1982 | Mirowski et al. |
| 4,375,817 A | | 3/1983 | Engle |
| 4,379,459 A | | 4/1983 | Stein |
| 4,384,585 A | | 5/1983 | Zipes |
| 4,556,063 A | | 12/1985 | Thompson et al. |
| 4,566,456 A | * | 1/1986 | Koning et al. ............... 600/488 |
| 4,577,633 A | | 3/1986 | Berkovits et al. |
| 4,587,970 A | | 5/1986 | Holley et al. |
| 4,708,143 A | * | 11/1987 | Schroeppel .................. 607/17 |
| 4,719,921 A | * | 1/1988 | Chirife ........................ 600/516 |
| 4,726,380 A | | 2/1988 | Vollmann |
| 4,727,877 A | | 3/1988 | Kallok |
| 4,730,619 A | * | 3/1988 | Koning et al. ............... 607/17 |
| 4,746,868 A | | 5/1988 | Davis |
| 4,800,883 A | | 1/1989 | Winstrom |
| 4,821,723 A | | 4/1989 | Baker et al. |
| 4,880,005 A | | 11/1989 | Pless et al. |
| 4,949,719 A | | 8/1990 | Pless et al. |
| 4,953,551 A | | 9/1990 | Mehra |
| 5,099,838 A | | 3/1992 | Bardy et al. |
| 5,117,824 A | | 6/1992 | Keimel |
| 5,144,949 A | | 9/1992 | Olson |
| 5,154,170 A | | 10/1992 | Bennett et al. |
| 5,158,078 A | | 10/1992 | Bennett et al. |
| 5,163,427 A | | 11/1992 | Keimel |
| 5,188,105 A | | 2/1993 | Keimel |
| 5,199,428 A | | 4/1993 | Obel et al. |
| 5,207,218 A | | 5/1993 | Carpentier |
| 5,226,413 A | | 7/1993 | Bennett et al. |
| 5,269,298 A | | 12/1993 | Adams et al. |
| 5,282,839 A | | 2/1994 | Roline et al. |
| 5,312,453 A | | 5/1994 | Shelton et al. |
| 5,314,340 A | | 5/1994 | Bardy et al. |
| 5,320,643 A | * | 6/1994 | Roline et al. .................. 607/11 |
| 5,330,507 A | | 7/1994 | Schwartz |
| 5,331,966 A | | 7/1994 | Bennett et al. |
| 5,354,316 A | | 10/1994 | Keimel |
| 5,368,040 A | | 11/1994 | Carney |
| 5,535,752 A | | 7/1996 | Halperin et al. |
| 5,545,186 A | | 8/1996 | Olson |
| 5,564,434 A | | 10/1996 | Halperin et al. |
| 5,626,623 A | | 5/1997 | Kieval et al. |
| 5,800,465 A | | 9/1998 | Maeda et al. |
| 5,810,735 A | | 9/1998 | Halperin et al. |
| 6,314,323 B1 | * | 11/2001 | Ekwall ........................ 600/513 |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

* cited by examiner

Primary Examiner—Mark Bockelman
(74) Attorney, Agent, or Firm—Thomas F. Woods; Eric R. Waldkoetier; Tom G. Berry

(57) ABSTRACT

Techniques for pacing the heart of a patient as a function of an intra-cardiac pressure make use of a pressure monitor that receives a pressure signal from a pressure sensor in the patient's right ventricle. The pressure monitor estimates the patient's pulmonary artery diastolic pressure. A rate-responsive pacemaker paces the patient's heart as a function of the estimated pulmonary artery diastolic pressure.

41 Claims, 11 Drawing Sheets

PRESSURE-MODULATED RATE-RESPONSIVE CARDIAC PACING

FIELD OF THE INVENTION

The present invention relates generally to cardiac pacemakers and cardiac monitoring, and particularly to rate-responsive cardiac pacemakers and pressure monitoring.

BACKGROUND

Heart failure refers to the heart's inability to keep up with the demands made upon it. Congestive heart failure refers to an inability of the heart to pump an adequate amount of blood to the body tissues. Because the heart is unable to pump an adequate amount of blood, blood returning to the heart becomes congested in the venous system.

In a healthy heart, the heart pumps all of the blood that returns to it, according to the Frank-Starling law. Increased venous return leads to increased end diastolic volume, which causes increased strength of contraction and increased stroke volume. In addition to intrinsic control according to the Frank-Starling law, a healthy heart is subject to extrinsic control, such as stimulation by the sympathetic nervous system to enhance contractility.

In a patient experiencing congestive heart failure, intrinsic and extrinsic control mechanisms may not function properly, and consequently the heart may fail to pump an adequate amount of blood. A condition known as cardiac decompensation is used to describe heart failure that results in a failure of adequate circulation.

Failure of the left side of the heart is generally more serious than the failure of the right side. On the left side of the heart, blood returns from the pulmonary system and is pumped to the rest of the body. When the left side of the heart fails, there are consequences to both the pulmonary system and to the rest of the body. A patient with congestive heart failure may be unable to pump enough blood forward to provide an adequate flow of blood to his kidneys, for example, causing him to retain excess water and salt. His heart may also be unable to handle the blood returning from his pulmonary system, resulting in a damming of the blood in the lungs and increasing his risk of developing pulmonary edema.

Increased blood pressure within the left side of the heart is usually attendant to failure of the left side of the heart. The increased pressure may be detected by an intra cardiac pressure sensor. The sensor may be implanted in the patient's right ventricle and may supply pressure signals to a monitor. The monitor may use pressure signals from the right ventricle to estimate the pressures in the left side of the heart.

Some patients with congestive heart failure benefit from an implanted pacemaker. A pacemaker rhythmically generates impulses that spread throughout the heart to drive the atria and ventricles. A typical pacemaker monitors the electrical activity of the patient's heart and provides pacing to cause the heart to beat at a desired rate, such as sixty beats per minute.

A rate-responsive pacemaker adjusts the pacing rate to the changing needs of the patient. For example, a rate-responsive pacemaker may normally pace the patient at sixty beats per minute when the patient is sleeping or a rest. When the patient increases his activity, however, the pacemaker may pace the patient's heart more rapidly to produce a higher heart rate. Rate-responsive pacemakers may sense changes in the patient's level of activity in various ways, such as by an accelerometer, by measuring the patient's blood temperature, by measuring the patient's oxygen saturation, and by measuring other biological factors.

Rate-responsive pacemakers are known in the art. In addition, techniques for monitoring intra cardiac pressures are known in the art. Examples of these techniques and/or devices may be found in the issued U.S. Patents listed in Table 1 below.

TABLE 1

| U.S. Pat. No. | Inventor | Issue Date |
| --- | --- | --- |
| 5,810,735 | Halperin et al. | Sep. 22, 1998 |
| 5,626,623 | Kieval et al | May 6, 1997 |
| 5,535,752 | Halperin et al. | Jul. 16, 1996 |
| 5,368,040 | Carney | Nov. 29, 1994 |
| 5,282,839 | Roline et al. | Feb. 01, 1994 |
| 5,226,413 | Bennett et al. | Jul. 13, 1993 |
| 5,158,078 | Bennett et al. | Oct. 27, 1992 |
| 5,154,170 | Bennett et al. | Oct. 13, 1992 |
| 4,003,379 | Ellinwood, Jr. | Jan. 18, 1977 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

As noted above, a typical rate-responsive pacemaker monitors the electrical activity of the patient's heart. The electrical activity reflects depolarization and repolarization of the heart, and does not reflect cardiac pressures. Furthermore, although rate-responsive pacemaking can treat cardiac decompensation, the electrical signals received by the pacemaker do not indicate whether cardiac decompensation is present or whether the patient is at risk of cardiac decompensation.

SUMMARY OF THE INVENTION

The present invention has certain objects. That is, various embodiments of the present invention provide solutions to one or more problems existing in the prior art with respect to treatment of cardiac decompensation in prior art pacemakers. In particular, it is an object of the present invention to treat cardiac decompensation by modulating a rate-responsive pacemaker with a signal based upon intra-cardiac pressures.

Accordingly, the present invention includes features that combine a rate-responsive pacemaker with a pressure sensor coupled to a pressure monitor. The pressure monitor receives the pressure signal from the sensor, and detects and/or estimates a particular pressure that is indicative of the patient's condition. This particular pressure is then used to generate a signal that causes the rate-responsive pacemaker to adjust the pacing of the patient's heart.

A pressure indicative of the patient's condition is the pressure in the right ventricle that causes the pulmonary valve to open. This pressure reflects the pulmonary artery diastolic pressure. The pulmonary artery diastolic pressure in turn reflects the average left atrium pressure for a cardiac cycle, and reflects the left ventricle filling pressure in diastole. During the phase when the pulmonary valve is forced open due to right ventricular ejection, the corresponding (estimated) pulmonary artery diastolic pressure (ePAD)

reflects the pulmonary capillary wedge (diastolic) pressure (PCWP), which reflects mean left atrial pressure (LAP), which reflects left ventricular end diastolic pressure (LVEDP).

Past studies on ePAD indicate that there is a very strong correlation between ePAD and PCWP. This relationship can be described as follows: ePAD reflects the PCWP≡mean LAP≡LVEDP. Note that ePAD≠PCWP, but that the two parameters have a fixed relationship: if PCWP increases, then the ePAD increases by the same increment, and if PCWP decreases, then the ePAD decreases by the same increment. Therefore, ePAD measurements made from the right side of the heart can be used to reflect left-sided left ventricular parameters, and in particular, the LVEDP.

Another feature of the invention, therefore, is a processor that monitors the pressure continuum in the right ventricle and identifies the pressure that corresponds to the estimated pulmonary artery diastolic pressure. This pressure is accurately indicative of pressures in the left side of the heart. The invention may include techniques for identifying the pressure in the right ventricle that is indicative of left side pressures.

Once the estimated pulmonary artery diastolic pressure is identified, the pressure may be used to generate a signal that is received by a rate-responsive pacemaker. The present invention includes a rate-responsive pacemaker that may be responsive to the electrical signals from the patient's heart and/or pressure signals from the patient's heart.

A further feature of the invention allows the patient's physician to customize the treatment for the patient. The patient's physician may specify, for example, suitable pacing for particular pressures. The present invention presents techniques whereby the patient's physician can relate the pacing of the patient's heart to the monitored pressures. The physician can further monitor the results of the patient's therapy.

In various embodiments, one or more of the features described above may provide a number of advantages. For example, cardiac decompensation can be diagnosed by the pressure monitor, and the cardiac decompensation can promptly be treated by a rate-responsive pacemaker. A further advantage is that the patient's estimated pulmonary artery diastolic pressure may be continually monitored, and the patient's pacing rate adjusted accordingly.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
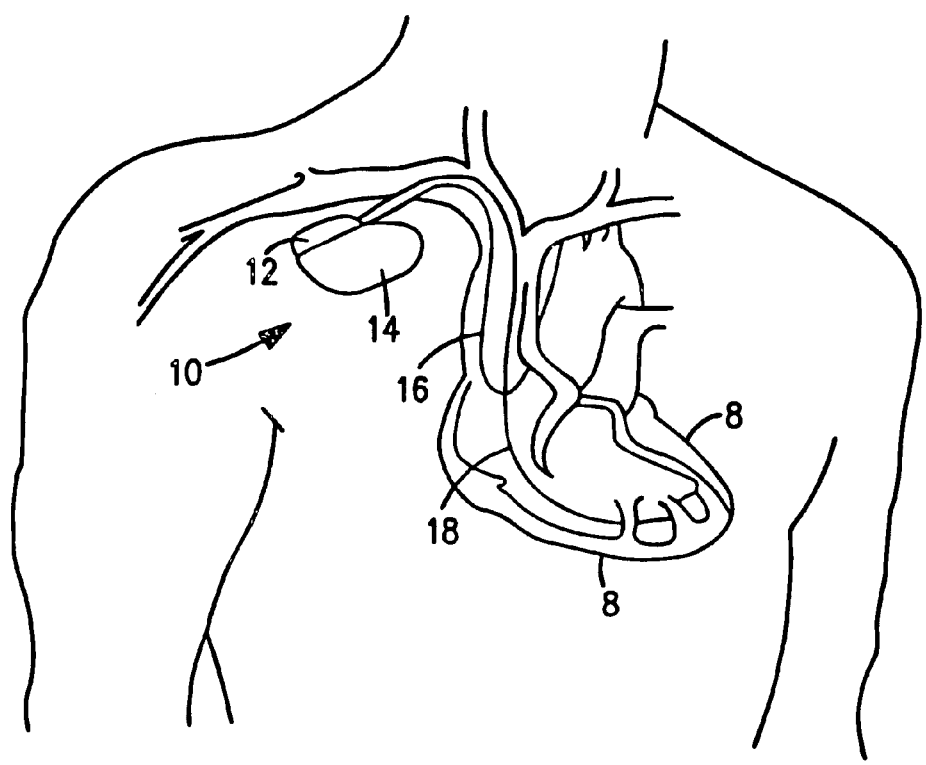
FIG. 1 is a schematic view of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8.

Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
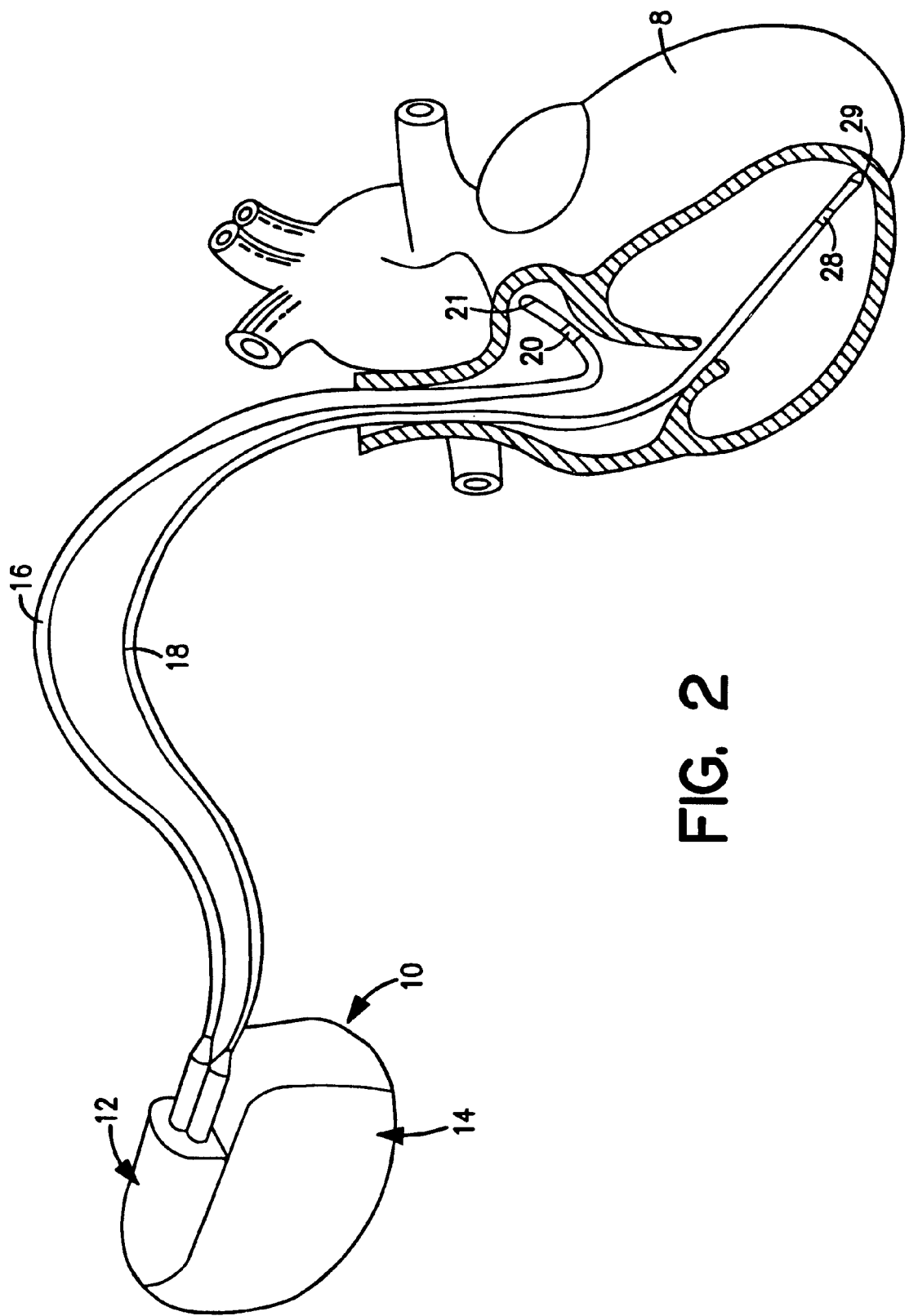
FIG. 2 shows the implantable medical device located in and near a heart.

FIG. 2 shows connector module 12 hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
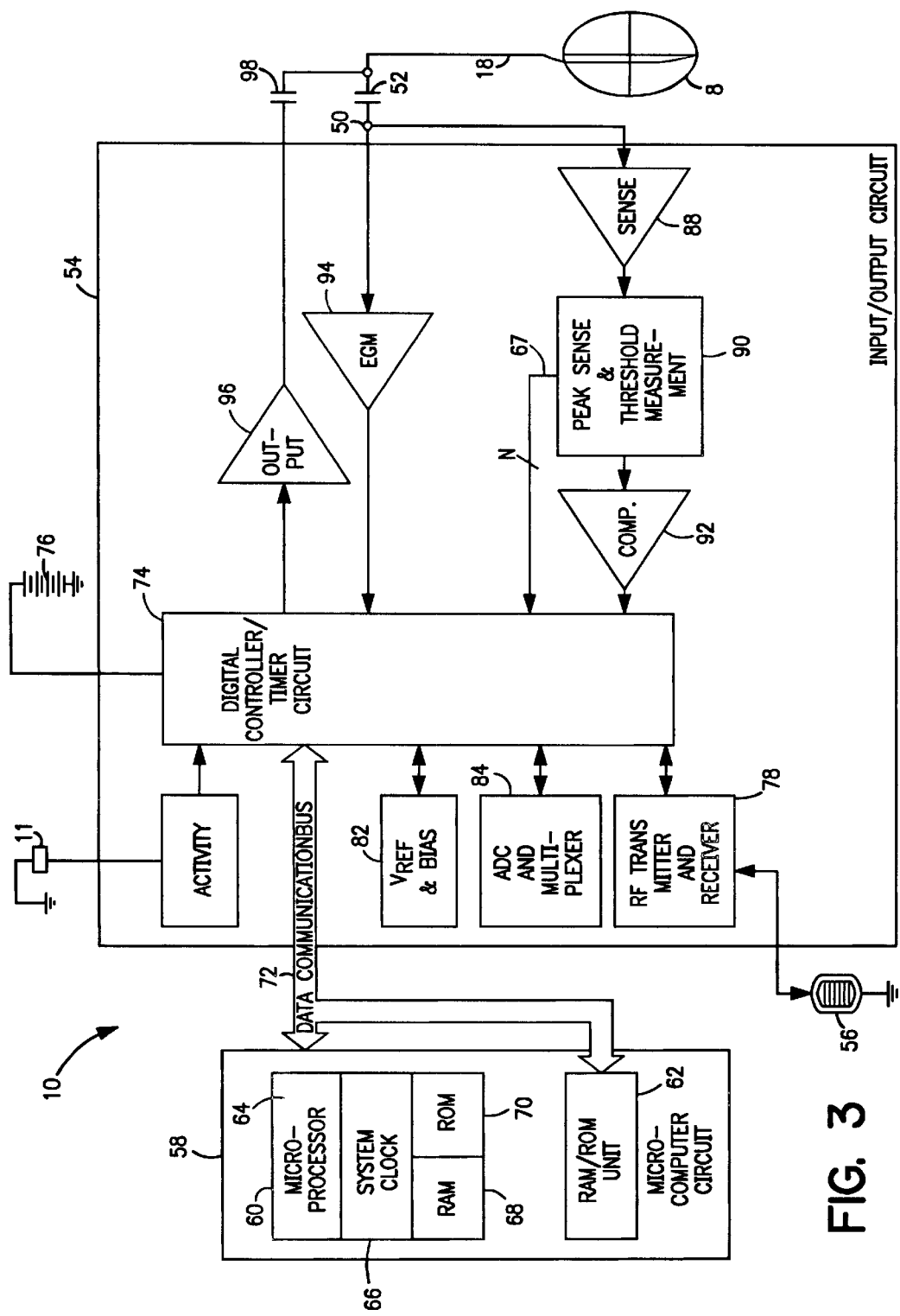
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto.

However, it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al's '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11 antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time"telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In preferred embodiments of the present invention, IMD 10 may operate in various rate-responsive modes, including, but not limited to, DDDR, DDIR, VVIR, VOOR and VVTR modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein. IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
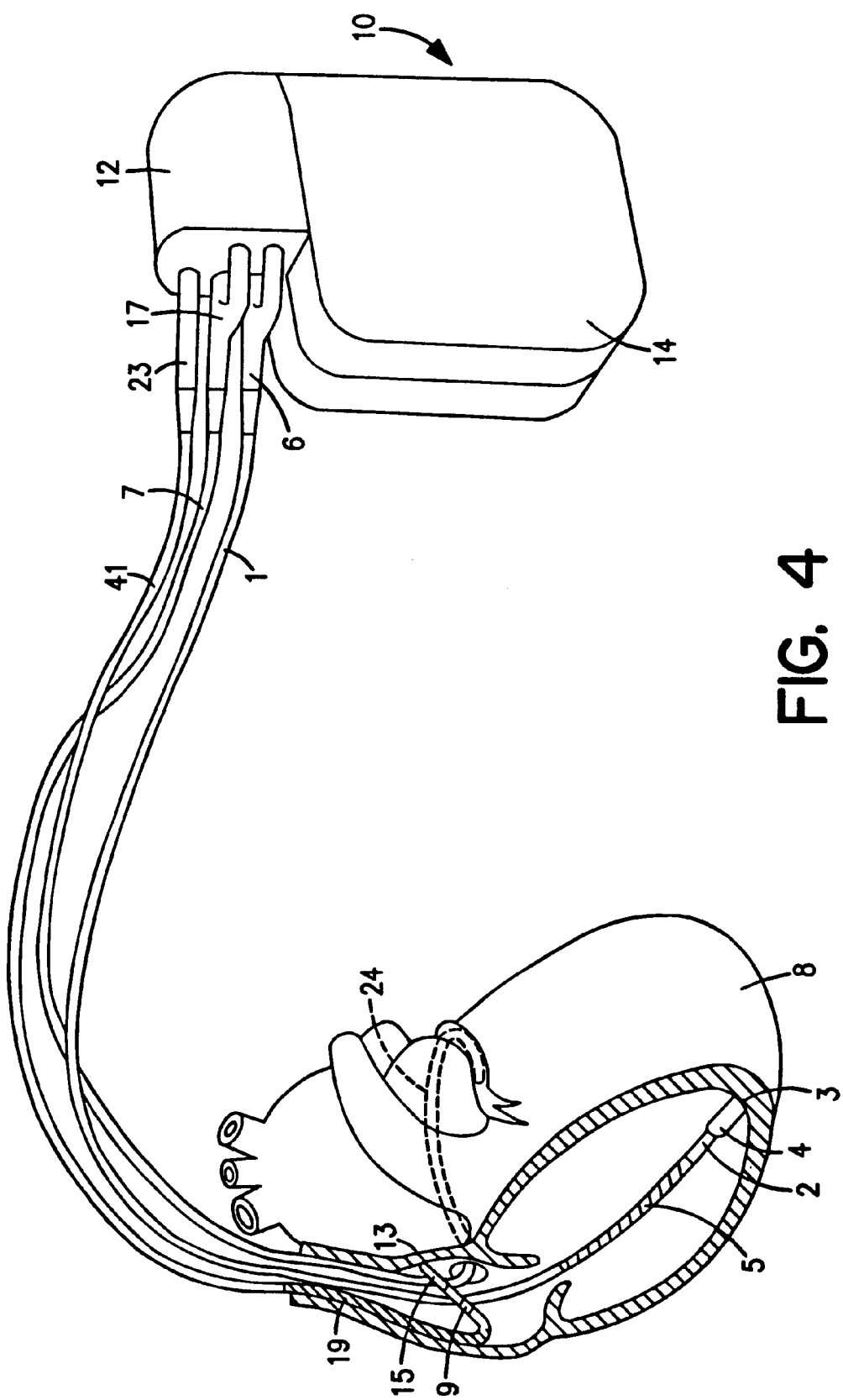
FIG. 4 shows a pacemaker-cardioverter-defibrillator located in and near a heart.
Figure 5:
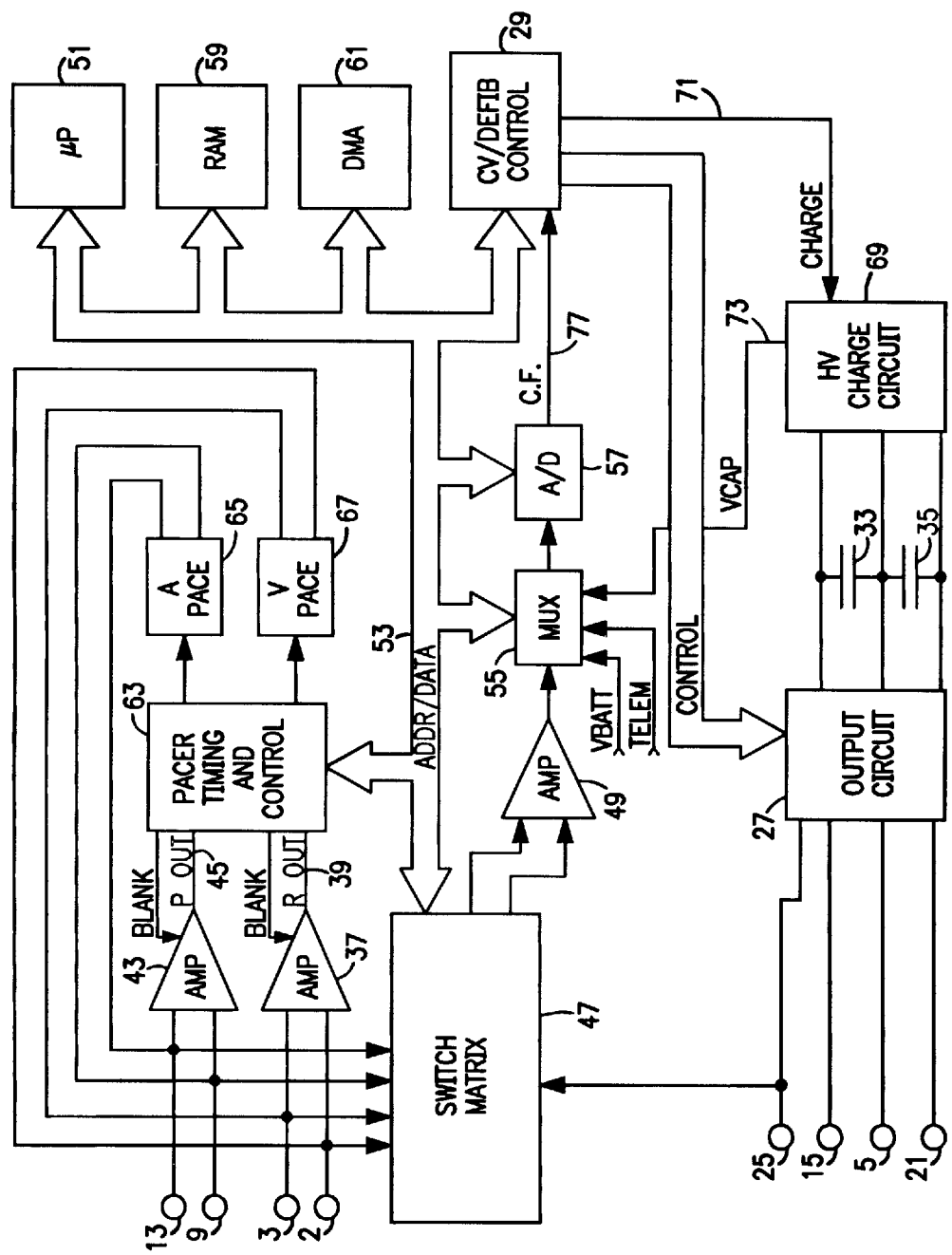
FIG. 5 is a functional schematic diagram of one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Elongated coil electrode 5, which is a defibrillation electrode 5, may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 24. Electrode 24, illustrated in broken outline in FIG. 4, is located within the coronary sinus and great vein of the heart. At the proximal end of the lead is connector plug 23 carrying an electrical connector coupled to the coiled conductor. Elongated coil defibrillation electrode 24 may be about 5 cm in length.

IMD 10 is shown in FIG. 4 in combination with leads 1, 7 and 41, and lead connector assemblies 23, 17 and 6 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies. IMD 10 is provided with an electrode system. If the electrode configuration of FIG. 4 is employed, the correspondence to the illustrated electrodes is as follows. Electrode 25 in FIG. 5 includes the uninsulated portion of the housing of NMD 10. Electrodes 25, 15, 24 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of a capacitor bank (which includes capacitors 33 and 35) during delivery of defibrillation pulses.

Electrodes 2 and 3 are located on or in the ventricle of the patient and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium of the patient and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824 to Keimel et al., hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by microprocessor 51 via data/address bus 53, which selections may be varied as desired. Signals from the electrodes selected for coupling to bandpass amplifier 49 are provided to multiplexer 55, and thereafter converted to multi-bit digital signals by AID converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time.

Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. W092/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726, 380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses. Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
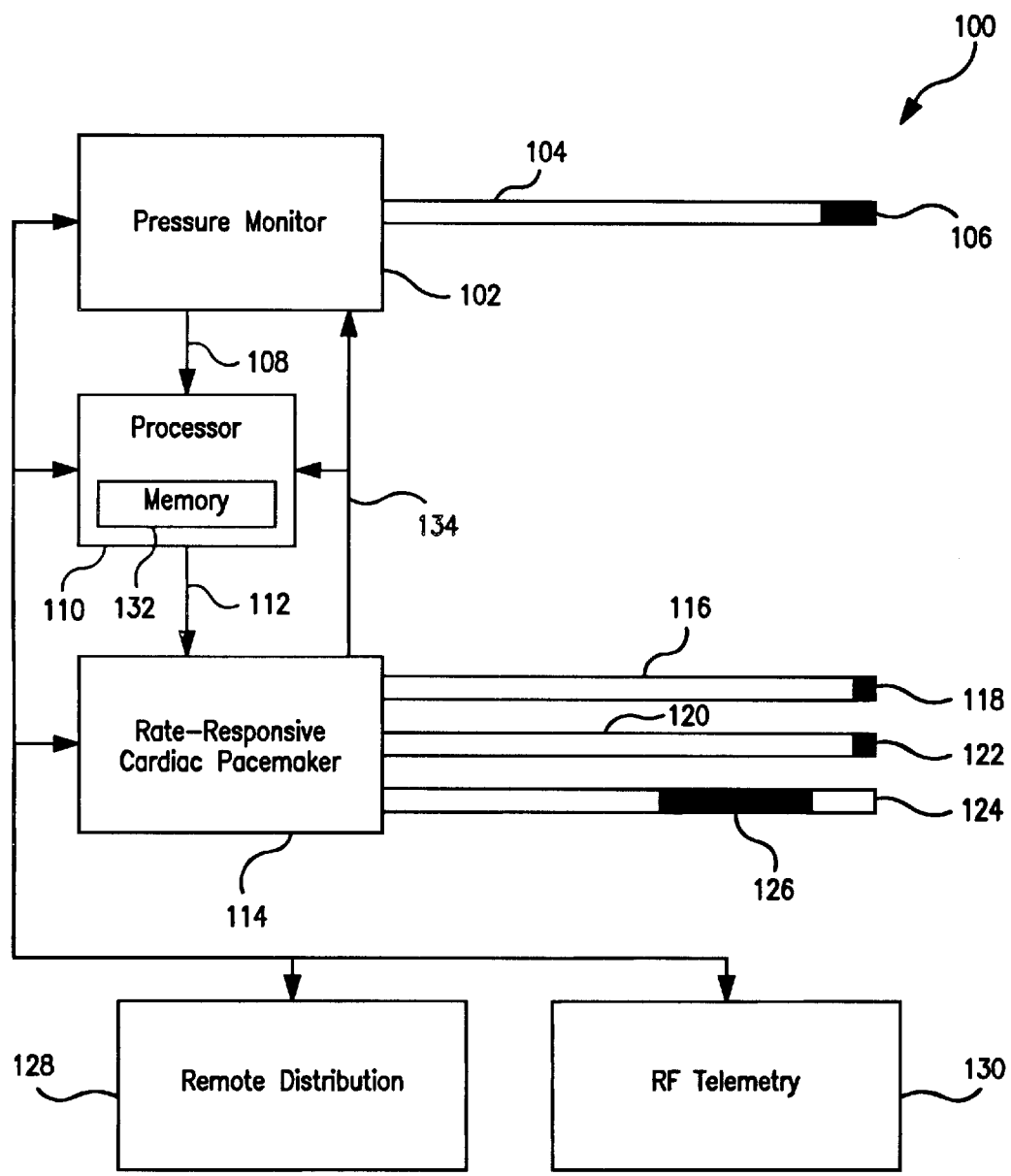
FIG. 6 is a diagram of a system including a pressure monitor and a rate-responsive cardiac pacemaker.

FIG. 6 shows a system 100 illustrating an embodiment of the invention, in which pressure is used to modulate pacemaker functions. System 100, which may be implantable in a human being or a mammal, includes rate-responsive cardiac pacemaker 114, which paces heart 8. Cardiac pacemaker 114 is coupled to atrial lead 116 and ventricular lead 120. Electrodes 118 and 122 disposed on leads 116 and 120 may serve to sense electrical signals and to pace heart 8. Pacemaker 114 may further be coupled to lead 124, which includes defibrillation coil electrode 126. Alternatively, defibrillation coil electrode 126 may be coupled to lead 116 or 120.

Pacmaker 114 may be one of the many forms of implantable medical devices described above. Atrial electrode 118 may correspond to any of electrodes 9, 13, 20 or 21 described above, ventricular electrode 122 may correspond to any of electrodes 2, 3, 28 and 29 described above, and defibrillation coil electrode 126 may correspond to elongated coil electrode 5 described above.

Importantly, pacemaker 114 is rate-responsive, i.e., pacemaker 114 can pace heart 8 at different rates, in response to conditions such as cardiac signals, control signals, signals from other components and/or programming. Typical rate-responsive pacemakers include members of the Thera™, Kappa™, InSync™ and InSync-ICD™ families of pacemakers manufactured by and commercially available from Medtronic, Inc., which incorporate, for example, AAIR, VVIR, VDDR and DDDR modes.

In general, a rate-responsive pacemaker adjusts the pacing rate to the changing needs of the patient. A rate-responsive pacemaker may normally pace the patient at sixty beats per minute, for example, when the patient is sleeping or a rest. When the patient increases his activity, however, the patient may require more rapid pacing to produce a higher heart rate.

Changes in the patient's level of activity have been sensed in various ways, such as by an accelerometer, by measuring the patient's blood temperature, by measuring the patient's oxygen saturation, and by measuring other biological factors. Devices measuring a change in activity may transmit signals to the pacemaker, which adjusts the pacing rate. The present invention presents techniques for adjusting pacing rates, based upon the pressure of the blood inside the patient's heart 8. System 100 includes pressure monitor 102, which is coupled to pressure sensor 106 by lead 104. Pressure sensor 106 responds to the absolute pressure inside heart 8.

Figure 7:
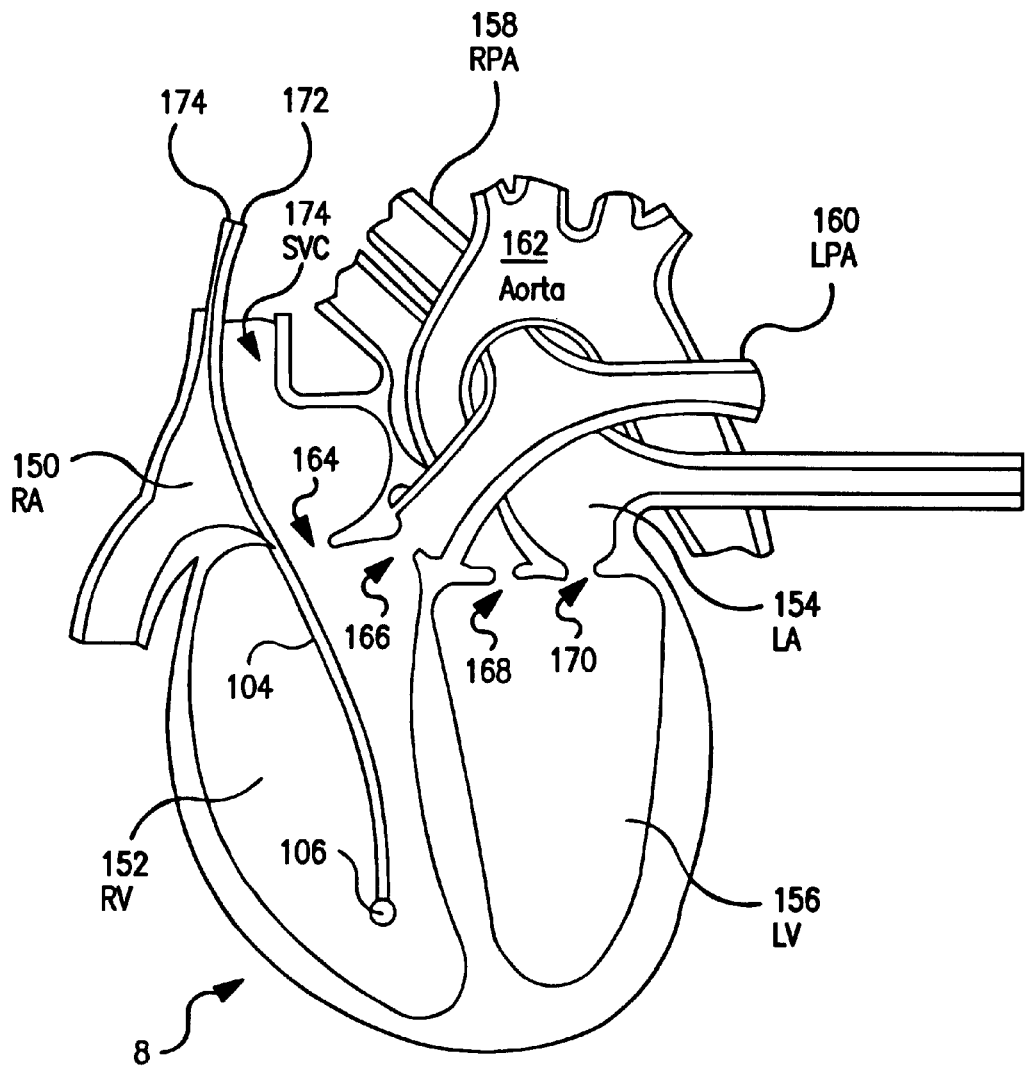
FIG. 7 is a diagram of a human heart, with a pressure sensor and a lead.

FIG. 7 is a diagram of a human heart, including a pressure sensor and a lead. In FIG. 7, sensor 106 is shown inside right ventricle 152 of heart 8. Sensor 106 is coupled to lead 104, which extends from right ventricle 152, through right atrioventricular valve 164, and through superior vena cava 174. Lead 104 extends further through the patient's circulatory system, eventually exiting the circulatory system and coupling to implanted pressure monitor 102 (not shown in FIG. 7). Pressure monitor 102 may be implanted in the patient's upper chest near pacemaker 114. Sensor may generate pressure signals itself or may modulate pressure signals conducted through lead 104 along wires 172 and 174. The pressure signals are a function of the fluid pressure in right ventricle 152. Pressure monitor 102 receives, monitors and analyzes the pressure signals, as will be described in more detail below. An example of pressure monitor 102 is the Chronicle™ Implantable Hemodynamic Monitor manufactured by and commercially available from Medtronic, Inc.

Pressure sensor 106 may be one of many forms of pressure sensors. One form of pressure sensor that is useful for measuring blood pressure inside a human heart is a capacitive absolute pressure sensor, as described in U.S. Pat. No. 5,564,434 to Halperin, et al., hereby incorporated by reference herein in its entirety. Pressure sensor 106 may also be a piezoelectric crystal or piezoresistive pressure transducer. The invention is not limited to any particular kind of pressure sensor.

As will be described below, pressure monitor 102 generates one or more processed pressure signals. Rate-responsive pacemaker 114 adjusts pacing activity as a function of one or more of the processed pressure signals.

A pressure of significance in patient-monitoring is the estimated pulmonary artery diastolic pressure (ePAD). As noted above, there is a strong correlation between ePAD and pulmonary capillary wedge pressure (PCWP), and ePAD closely reflects PCWP.

In systole, ventricles 152 and 156 contract. For a brief period, no blood leaves ventricles 152 and 156, and the contraction is isovolumetric. During isovolumetric contraction, atrioventricular valves 164 and 170 are closed by backward pressure differential forces. Aortic valve 168 and pulmonary valve 166 are likewise closed, as the pressure in ventricles 152 and 156 is insufficient to force blood through them.

Consequently, isovolumetric contraction causes the blood in ventricles 152 and 156 to undergo increasing pressure. In a short time, the pressure in right ventricle 152 overcomes the pressure in pulmonary arteries 158 and 160, pulmonary valve 166 is driven open, and blood is ejected from right ventricle into pulmonary arteries 158 and 160. Similarly, the pressure in left ventricle 156 overcomes the pressure in aorta 162, driving open aortic valve 168 and ejecting blood into aorta 162. The pressure needed to open aortic valve 168 is normally much higher than the pressure needed to open pulmonary valve 166.

The pressure needed to open pulmonary valve 166 is, for practical purposes, an accurate measure of ePAD. ePAD reflects the average pressure in left atrium 154 over a cardiac cycle, also called the mean LAP. In addition, ePAD reflects the filling pressure in left ventricle 156 during diastole, also called the left ventricular end diastolic pressure or LVEDP. In a healthy heart, LAP and LVEDP range from approximately 8 mm Hg to 12 mm Hg. ePAD may be somewhat higher than LAP and LVEDP, but past studies indicate a strong correlation between ePAD and PCWP, mean LAP and LVEDP. In a heart having congestive heart failure, each of these pressures may be considerably elevated, as will be discussed below.

Mean LAP and LVEDP are pressures on the left side of heart 8. Practical considerations make it difficult to measure pressures on the left side of heart 8 directly. These pressures may be measured indirectly, however, by placing sensor 106 in right ventricle 152 and measuring ePAD with pressure monitor 102.

Measurement of ePAD is not equivalent to measuring the highest pressure in right ventricle 152. During isovolumetric contraction in systole, the pressure in right ventricle 152 increases and forces pulmonary valve 166 open. Pressure in right ventricle 152 does not peak at this point, however. Rather, pressure in right ventricle 152 increases during ejection as well, but the pressure increases at a reduced rate.

Figure 8:
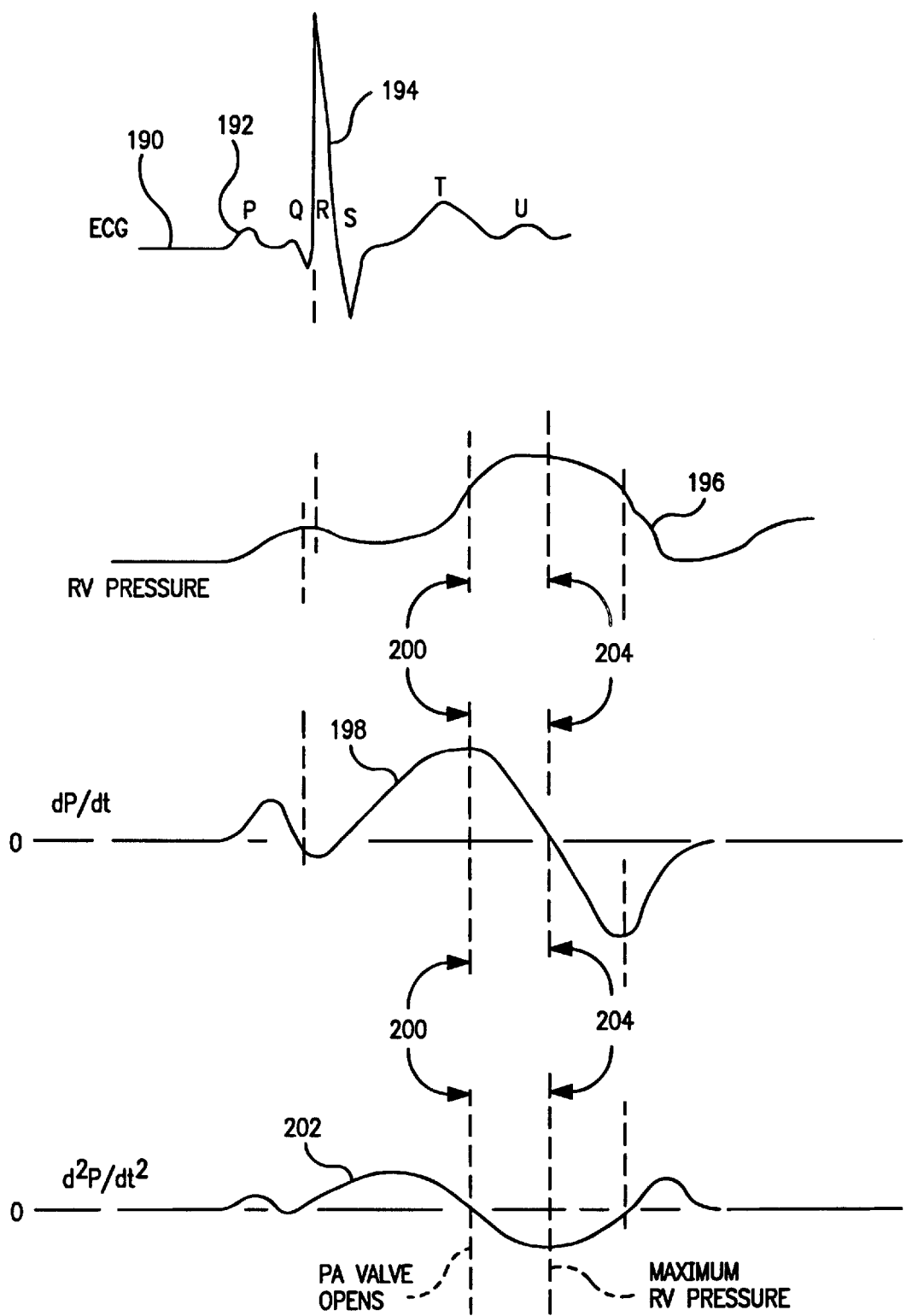
FIG. 8 shows a typical electrocardiogram signal and a typical signal indicative of right ventricular pressure, and the first and second derivatives of the right ventricular pressure signal.

It is this change in the rate of increase of pressure that helps identify ePAD, as illustrated in FIG. 8. Pressure signal 196 from sensor 106 in right ventricle 152 is shown in reference to standard electrocardiogram (ECG) signal 190. ECG signal 190 may be sensed by electrodes 118 and/or 122, and provided as ECG signal 134 to pressure monitor 102 and/or processor 110.

R-wave 194 in ECG signal 190 represents ventricular depolarization of heart 8. Following ventricular depolarization, pressure in right ventricle 152 increases, eventually reaching a peak pressure 204.

When the pressure in right ventricle 152 overcomes the pressure in pulmonary arteries 158 and 160, pulmonary valve 166 is driven open. When pulmonary valve 166 opens, contraction is no longer isovolumetric. Pressure in right ventricle 152, although still increasing due to ventricular contraction, increases at a slower rate. As a result, there is an inflection point 200 in pressure signal 196 when pulmonary valve 166 opens.

Inflection point 200 may be found by taking the first derivative of right ventricular pressure with respect to time, or dP/dt. Because the slope of pressure signal 196 is at its maximum at inflection point 200, curve 198 of dP/dt peaks at inflection point 200. Inflection point 200 may also be found by finding the point on right ventricular pressure curve 196 corresponding to the maximum value of dP/dt. Inflection point 200 may also be found by taking the second derivative of right ventricular pressure with respect to time, or $d^2P/dt^2$. The point on right ventricular pressure curve 196 at which curve 202 of $d^2P/dt^2$ goes negative for the first time after R-wave 194 is inflection point 200.

Pressure monitor 102 may include differentiating circuits that generate $d^2P/dt^2$ curve 202 and/or dP/dt curve 198. Pressure monitor 102 may further include circuits to detect when $d^2P/dt^2$ curve 202 crosses zero or when dP/dt curve 198 peaks, both of which occur at inflection point 202. By detecting inflection point 202, pressure monitor 102 may measure the pressure in right ventricle 152 at inflection point 202. The pressure at inflection point 202 is ePAD.

Figure 9:
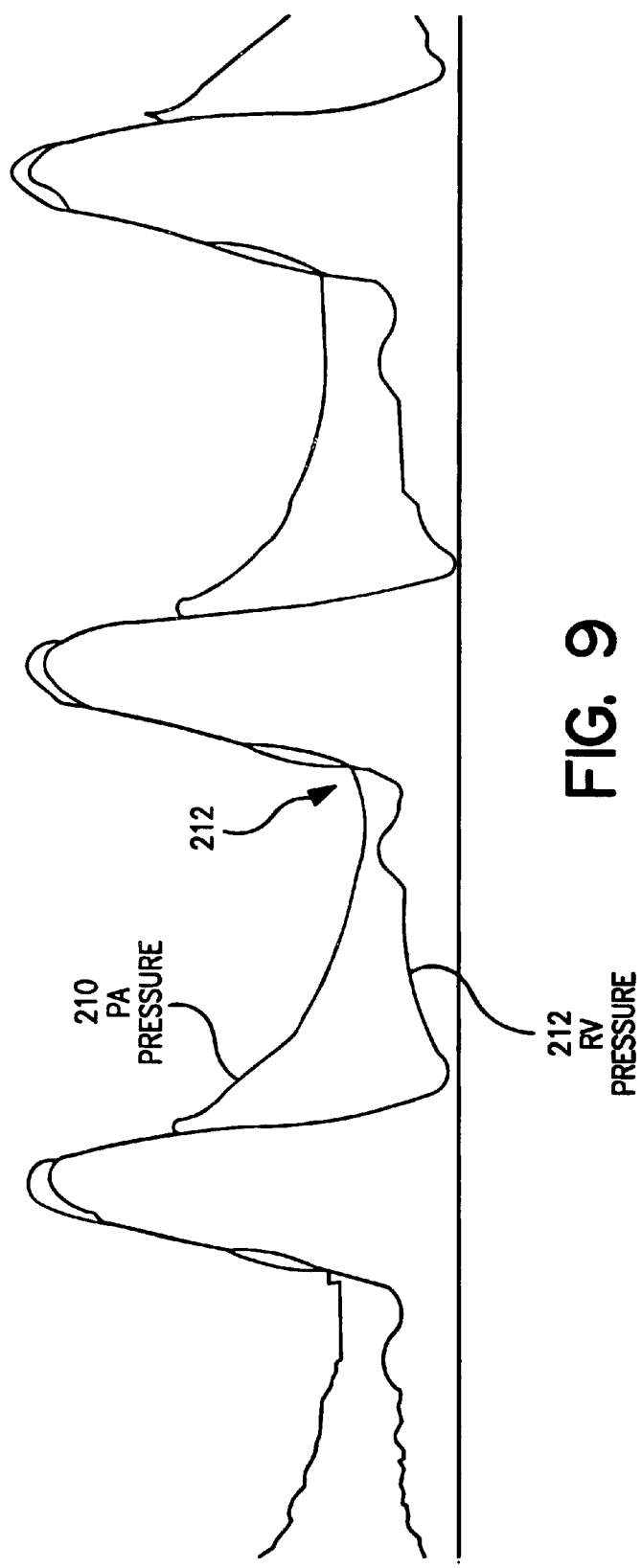
FIG. 9 shows right ventricular pressure charted in relation to pulmonary artery pressure.

FIG. 9 shows right ventricle pressure curve 212 superimposed on pulmonary artery pressure curve 210. As shown in FIG. 9, the minimum pulmonary artery diastolic pressure is nearly equal to the right ventricle pressure at point 212, when curves 210 and 212 cross each other. This pressure is ePAD, the pressure at which the pressure in right ventricle 152 overcomes the pressure in pulmonary arteries 158 and 160, opening pulmonary valve 166. ePAD is a significant pressure in many respects. Patients having chronic congestive heart failure often exhibit elevated ePAD levels. In particular, elevated ePAD levels are frequently present in patients having advanced cardiac disease and often dilated cardiomyopathy or restrictive cardiomyopathy. Hearts of patients having congestive heart failure often fail to achieve adequate circulation, a condition known as cardiac decompensation.

One factor contributing to cardiac decompensation is pulmonary edema, in which excess tissue fluid enters the lungs. The fluid accumulation in the lungs reduces the oxygen-carbon dioxide exchange, leading to an elevation of acid-forming carbon dioxide in the blood. Pulmonary edema is caused by overloading of the heart, i.e., an inability of the heart to expel the blood being returned to it. When blood is unable to return to the heart from the pulmonary system, the blood dams up in the lungs, and pulmonary edema results.

Cardiac decompensation and pulmonary edema can be serious. In many cases, the conditions require intensive care and hospitalization. Cardiac decompensation and pulmonary edema can be fatal.

Patients having congestive heart failure are at risk of pulmonary edema. The damming of the blood in the lungs leads to increased pressure in the pulmonary circulatory system, which results in an elevated pulmonary artery pressure. Elevated pulmonary artery pressure is therefore a sign of risk of pulmonary edema.

Because ePAD is a close approximation of pulmonary artery pressure, ePAD is also a sign of risk of pulmonary edema. In general, as a patient's PCWP approaches approximately 24 mm Hg, the patient's risk of pulmonary edema increases. When a patient's PCWP exceeds 24 mm Hg, pulmonary edema is very likely to occur.

One way to reduce the risk of pulmonary edema is to move more blood through the heart, i.e., decrease overloading by increasing cardiac output (CO). CO is defined as the volume of blood pumped by each ventricle per minute. CO is determined by two factors: heart rate (HR) in units of beats per minute, and stroke volume (SV) in units of volume of blood pumped per stroke, i.e., per beat. The relationship between CO, HR and SV is usually expressed:

$$CO = HR \times SV$$

Increasing CO causes more blood to be expelled from the heart, which reduces overloading and reduces the damming of the blood in the lungs. Increasing CO can therefore cause pulmonary artery pressure, and the risk of pulmonary edema, to decrease.

One way to increase CO, is to increase HR, i.e., cause the heart to beat faster. One technique for causing the heart to beat faster is to pace the heart more rapidly using rate-responsive cardiac pacemaker 114.

Figure 10:
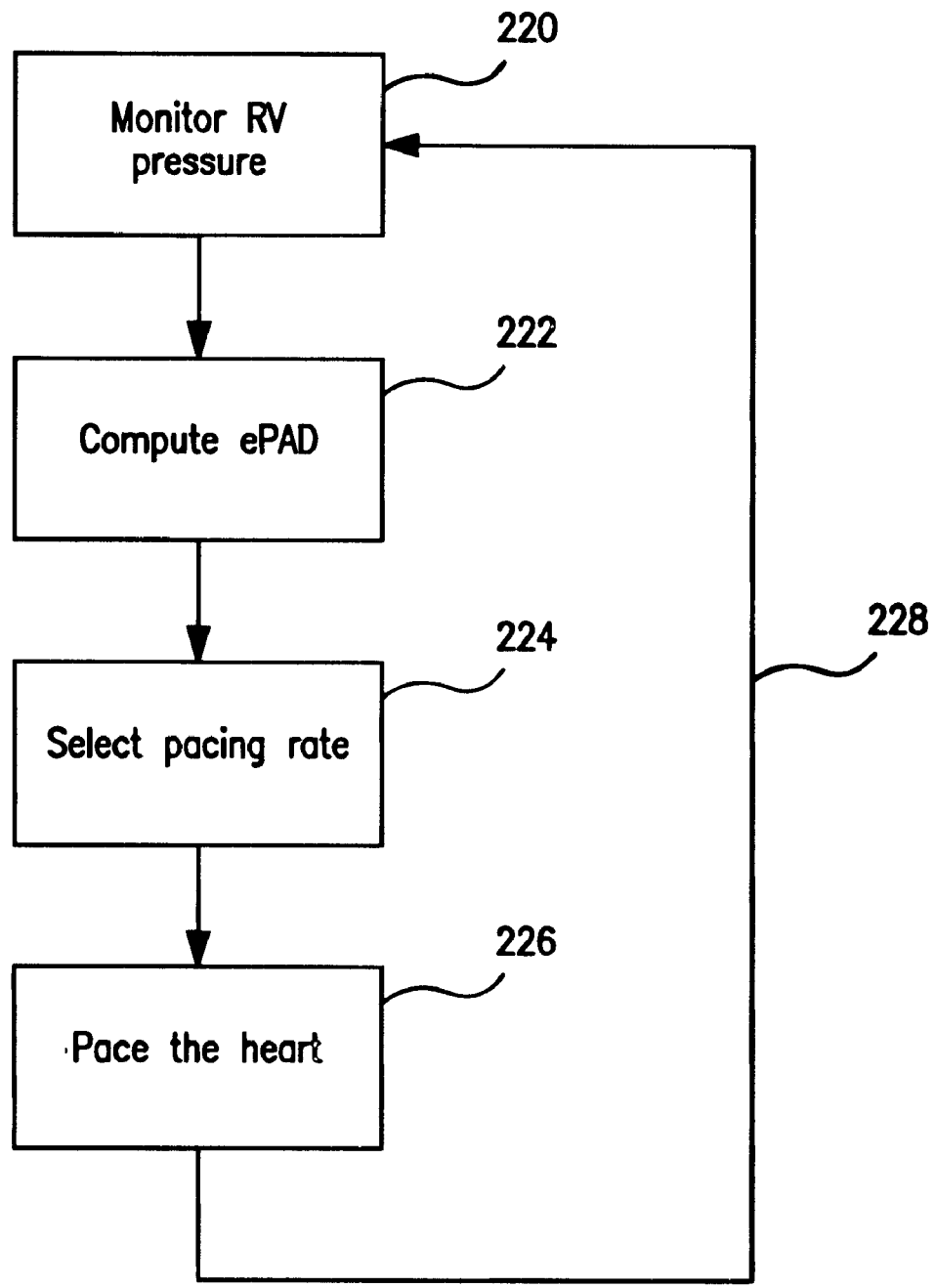
FIG. 10 is a flow diagram illustrating techniques of the invention.

Techniques for pressure-based pacing are shown in FIG. 10. Pressure monitor 102 monitors the pressure in right ventricle 152 via pressure sensor 106 coupled to lead 104 (220). From these pressure measurements, pressure monitor 102 computes ePAD using techniques described above (222). Pressure monitor 102 generates ePAD signal 108, which is received by processor 110.

Processor 110 selects a pacing rate as a function of ePAD signal 108 (224) and generates control signal 112, which is received by pacemaker 114. Pacemaker 114 paces heart 8 as a function of control signal 112 (226). When pressure monitor 102 computes an elevated ePAD, for example, processor 110 may generate control signal 112 resulting in a higher pacing rate by pacemaker 114, and consequently a higher heart rate. A higher heart rate results in increased cardiac output and reduced risk of pulmonary edema.

The results of the rate-responsive pacing may be reflected in the patient's ePAD, which may be used for further rate-responsive pacing. The rate of pacing can then be readjusted based upon the patient's ePAD. Thus, system 100 may use feedback continually to monitor the patient's ePAD and adjust the patient's pacing rate (228).

Processor 110 may be housed inside pressure monitor 102, in pacemaker 114, or separately from both pressure monitor 102 and pacemaker 114.

Data pertaining to a patient's ePAD may be stored in memory 132. The data may reflect the patient's ePAD on a beat-to-beat basis, a minute-to-minute basis, an hour-to-hour basis, or on some other basis.

The patient's ePAD data may thereafter be retrieved via input/output devices such as remote distribution link 128 or RF telemetry 130. The data can then be plotted for viewing by a physician. Remote distribution link 128 provides a channel for downloading data from the patient over a telephone line or over the internet, for example. RF telemetry 130 provides immediate access to the data on a dedicated channel. Typically, a patient is required to visit the physician's office when data are to be downloaded via RF telemetry 130.

Input/output devices 128 and 130 allow a person such as the patient's physician to exchange information with processor 110, pressure monitor 102 and/or pacemaker 114. The information exchanged may include not only pressure data, but pacing data, patient activity data, and other numbers, statistics or data.

The information exchanged may also include programming. Processor 110 may be programmable by a physician via input/output devices 128 and 130. Memory 132 may be used to store the instructions programmed by the physician. The programming may reflect, for example, the physician's judgment as to the pressure-based rate-responsive pacing appropriate for the patient.

Figure 11:
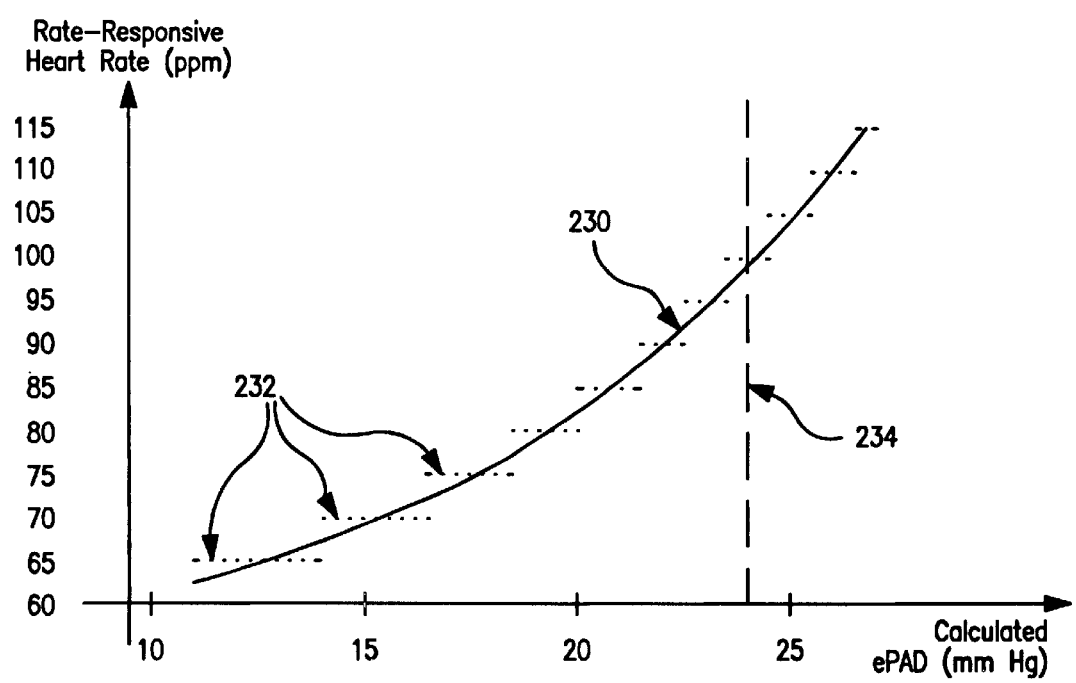
FIG. 11 is a graph showing an illustrative relation between a patient's estimated pulmonary artery diastolic pressure and the rate-responsive heart rate.

FIG. 11 is a graph illustrating an exemplary relationship between ePAD and paced heart rate in paces per minute. Curve 230 defines the appropriate pacing rate as a function of the patient's calculated ePAD. Curve 230 may be defined by an equation that applies over a range of ePAD values, the equation being of the general form pacing rate =f(ePAD).

As shown in FIG. 11., the pacing rate increases non-linearly as the patient's ePAD approaches 24 mm Hg (234). The increase in slope of curve 230 represents a rapid increase in pacing when the patient is at risk of pulmonary edema. The rapid pacing causes HR to rise, consequently boosting CO, thereby alleviating the overloading and reducing the risk of pulmonary edema.

Pacing can be adjusted for a defined number of cardiac cycles, on a beat-to-beat basis, a minute-to-minute basis, or on some other basis. Although curve 230 in the graph in FIG. 11 defines pacing values corresponding to an ePAD of about 11 mm Hg or greater, the physician may program pacing rates corresponding a narrower range of ePAD values. For example, the physician may feel that, for a particular patient, pacing responsive to ePAD is indicated only if the patient's ePAD exceeds 20 mm Hg, so there will pacing rates corresponding to any ePAD above 20 mm Hg, but there will be no pacing rates corresponding to any ePAD below 20 mm Hg.

The physician may describe the dependence of rate-responsive pacing upon ePAD as a curve, or as an equation that defines a curve. The physician may also describe the correspondence in other ways. The physician may, for example, program discrete pacing rates for discrete values of ePAD. FIG. 11 shows one such correlation between discrete ePAD values and discrete rate-responsive pacing, resulting in a piecewise linear relationship (232). The subset of ePAD values between 14 mm Hg and 16 mm Hg, for example, corresponds to a pacing rate of 70 paces per minute. Similarly, other subsets of ePAD values correspond to a single pacing rate.

As another alternative, the correspondence between ePAD and rate-responsive pacing may also be stored in memory 132 as a table of values. Processor 110 then finds a pacing rate corresponding to an ePAD by looking up the pacing rate in the table.

The shape of curve 230 and piecewise linear relationship 232 shown in FIG. 11 are for purposes of illustration. How pacing corresponds to ePAD may depend upon the patient's particular needs. For one patient, the relationship may be, for example, linear throughout the ePAD range. For another patient, the relationship may be exponential. For yet another patient, the relationship may resemble an S-shaped curve.

The preceding specific embodiments are illustrative of the practice of the invention. It is to be understood, therefore, that other expedients known to those skilled in the art or disclosed herein may be employed without departing from the invention or the scope of the claims. For example, rate-responsive pacemaker 114 may be responsive to inputs in addition to ePAD-based control signal 112, such as electrical signals sensed by electrodes 118 and 122, or signals from an accelerometer.

The invention further includes within its scope the methods of making and using the systems described above. These methods are not limited to the specific examples described above, but may be adapted to meet the needs of a particular patient. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A system comprising:
 a pressure sensor that generates a first signal as a function of pressure in a heart;
 a pressure monitor that estimates pulmonary artery diastolic pressure as a function of the first signal, and generates a second signal as a function of the estimated pulmonary artery diastolic pressure; and a pacemaker that paces the heart at a rate that is a function of the second signal.

2. The system of claim 1, wherein the pressure sensor is disposed in the right ventricle of the heart.

3. The system of claim 1, wherein the pressure monitor comprises a differentiating circuit, the differentiating circuit configured to generate a differential signal representative of the first derivative of the first signal, wherein the pressure monitor estimates pulmonary artery diastolic pressure as a function of the differential signal.

4. The system of claim 1, wherein the pressure monitor comprises a differentiating circuit, the differentiating circuit configured to generate a differential signal representative of the second derivative of the first signal, wherein the pressure monitor estimates pulmonary artery diastolic pressure as a function of the differential signal.

5. The system of claim 1, wherein the system is implantable in a human body.

6. The system of claim 1, further comprising a sensing lead coupled to the pacemaker, the sensing lead configured to sense electrical signals attendant to the depolarization and repolarization of the heart.

7. The system of claim 1, further comprising a processor, the processor configured to compute a pacing rate for the pacemaker as a function of the second signal.

8. The system of claim 7, wherein the processor is further configured to generate a control signal as a function of the pacing rate, and wherein the pacemaker is further configured to receive the control signal and to pace the heart as a function of the control signal.

9. The system of claim 7, further comprising an input/output device coupled to the processor, the input/output device configured to exchange information between a person and the processor.

10. The system of claim 1, wherein the pressure sensor is selected from a group consisting of a capacitive absolute pressure sensor a piezoelectric crystal transducer and a piezoresistive pressure transducer.

11. A method comprising:

receiving a pressure signal, the pressure signal being a function of the pressure in the right ventricle of a heart;

estimating the pulmonary artery diastolic pressure as a function of the pressure signal; and pacing the heart at a rate that is a function of the estimated pulmonary artery diastolic pressure.

12. The method of claim 11, wherein estimating the pulmonary artery diastolic pressure comprises:

generating the first derivative of the pressure signal during a cardiac cycle;

sensing the point on the pressure signal at which the first derivative of the pressure signal is maximized; and adopting as the estimated pulmonary artery diastolic pressure the pressure at the point on the pressure signal at which the first derivative of the pressure signal is maximized.

13. The method of claim 11, wherein estimating the pulmonary artery diastolic pressure comprises:

sensing an R-wave of a cardiac cycle;

taking the second derivative of the pressure signal during the cardiac cycle;

sensing the point on the pressure signal at which the second derivative of the pressure signal becomes negative after the R-wave; and adopting as the estimated pulmonary artery diastolic pressure the pressure at the point on the pressure signal at which the second derivative of the pressure signal becomes negative after the R-wave.

14. The method of claim 11, further comprising:

storing a range of estimated pulmonary artery diastolic pressure values and a pacing rate value corresponding to each estimated pulmonary artery diastolic pressure value in the range;

determining a pacing rate that corresponds to the estimated pulmonary artery diastolic pressure; and pacing the heart at the pacing rate.

15. The method of claim 14, further comprising:

receiving a range of estimated pulmonary artery diastolic pressure values; and receiving a corresponding pacing rate value for each estimated pulmonary artery diastolic pressure value in the range.

16. The method of claim 15, further comprising storing the received range of estimated pulmonary artery diastolic pressure values and the corresponding pacing rate values in memory.

17. The method of claim 15, wherein the estimated pulmonary artery diastolic pressure values correspond to the pacing rate values according to an equation that defines a curve.

18. The method of claim 11 further comprising pacing the heart when the estimated pulmonary artery diastolic pressure exceeds 20 mm Hg.

19. A system comprising:

a pressure monitor configured to receive a pressure signal, the pressure signal varying as a function of the pressure of blood in the left ventricle of a patient; and a pacemaker coupled to the pressure monitor configured to pace the heart, wherein the pressure monitor is configured to estimate the pulmonary artery diastolic pressure as a function of the pressure signal, and wherein the pacemaker is configured to pace the heart at a rate that is a function of the estimated pulmonary artery diastolic pressure.

20. The system of claim 19, further comprising a pressure sensor coupled to the pressure monitor and disposed inside the right ventricle of the heart of a patient, the pressure sensor configured to generate a pressure signal as a function of the pressure in the right ventricle.

21. The system of claim 19, wherein the system is implantable in a human body.

22. The system of claim 19, further comprising a sensing lead coupled to the pacemaker, the sensing lead configured to sense electrical signals attendant to the depolarization and repolarization of the heart.

23. The system of claim 19, further comprising a processor coupled to the pressure monitor and to the pacemaker, the processor configured to compute a pacing rate as a function of the estimated pulmonary artery diastolic pressure.

24. A method of pacing the heart of a patient, the method comprising:

implanting in the right ventricle of the patient a pressure sensor configured to generate a pressure signal as a function of the pressure in the right ventricle;

implanting in the patient a pressure monitor coupled to the pressure sensor, the pressure monitor configured to receive the pressure signal and to estimate the pulmonary artery diastolic pressure as a function of the pressure signal;

implanting in the patient a processor coupled to the pressure monitor, the processor configured to compute a pacing rate as a function of the estimated pulmonary artery diastolic pressure;

implanting in the patient a pacemaker coupled to the processor;

monitoring the estimated pulmonary artery diastolic pressure of the patient using the pressure sensor and the pressure monitor;

selecting a pacing rate as a function of the estimated pulmonary artery diastolic pressure; and pacing the heart as a function of the pacing rate.

25. The method of claim 24, further comprising implanting in the patient a sensing lead coupled to the pacemaker, the sensing lead configured to sense electrical signals attendant to the depolarization and repolarization of the heart.

26. The method of claim 25, further comprising pacing the heart as a function of the electrical signals sensed by the sensing lead.

27. The method of claim 24, further comprising:

defining a range of estimated pulmonary artery diastolic pressure values;

for each estimated pulmonary artery diastolic pressure value in the range, assigning a corresponding pacing rate value;

storing the range of estimated pulmonary artery diastolic pressure values and the corresponding pacing rate values in memory of at least one of the pressure monitor, processor and pacemaker.

28. The method of claim 27, wherein assigning a corresponding pacing rate comprises defining an equation that relates a pacing rate to an estimated pulmonary artery diastolic pressure.

29. A method comprising:

receiving an estimated pulmonary artery diastolic pressure; and selecting a pacing rate as a function of the estimated pulmonary artery diastolic pressure.

30. The method of claim 29, further comprising pacing the heart as a function of the pacing rate.

31. The method of claim 29, further comprising computing a pacing rate according to a pre-selected equation.

32. The method of claim 29, further comprising selecting a pacing rate from a lookup table.

33. The method of claim 29, further comprising:

determining a range of pulmonary artery diastolic pressure values into which the estimated pulmonary artery diastolic pressure falls; and selecting the pacing rate corresponding to the range.

34. The method of claim 29, further comprising:

receiving an electrocardiogram signal;

selecting the pacing rate as a function of the electrocardiogram signal.

35. The method of claim 29, further comprising transmitting the pacing rate to a pacemaker.

36. The method of claim 29, wherein the estimated pulmonary artery diastolic pressure is a first estimated pulmonary artery diastolic pressure and the pacing rate is a first pacing rate, the method further comprising:

receiving a second estimated pulmonary artery diastolic pressure; and selecting a second pacing rate as a function of the second estimated pulmonary artery diastolic pressure.

37. A system comprising:

means to sense the pressure in a heart;

means for estimating pulmonary artery diastolic pressure as a function of the pressure in the heart; and means for pacing the heart at a rate that is a function of the estimated pulmonary artery diastolic pressure.

38. The system of claim 37, wherein the means to sense the pressure in a heart is disposed in the right ventricle of the heart.

39. The system of claim 37, wherein the system is implantable in a human body.

40. The system of claim 37, means to sense electrical signals attendant to the depolarization and repolarization of the heart.

41. The system of claim 37, further comprising means for computing a pacing rate as a function of the estimated pulmonary artery diastolic pressure.

* * * * *